(12) United States Patent
Xu et al.

(10) Patent No.: US 11,534,137 B2
(45) Date of Patent: Dec. 27, 2022

(54) ULTRASOUND PROBE ASSEMBLY AND METHOD USING THE SAME

(71) Applicants: HEFEI BOE OPTOELECTRONICS TECHNOLOGY CO., LTD., Anhui (CN); BOE TECHNOLOGY GROUP CO., LTD., Beijing (CN)

(72) Inventors: Jinbo Xu, Beijing (CN); Hongqiao Xu, Beijing (CN)

(73) Assignees: HEFEI BOE OPTOELECTRONICS TECHNOLOGY CO., LTD., Anhui (CN); BOE TECHNOLOGY GROUP CO., LTD., Beijing (CN)

( * ) Notice: Subject to any disclaimer, the term of this patent is extended or adjusted under 35 U.S.C. 154(b) by 188 days.

(21) Appl. No.: 16/534,542

(22) Filed: Aug. 7, 2019

(65) Prior Publication Data

US 2020/0129146 A1  Apr. 30, 2020

(30) Foreign Application Priority Data

Oct. 30, 2018 (CN) .......................... 201821769998.1

(51) Int. Cl.
*A61B 8/00* (2006.01)
*A61B 8/12* (2006.01)
*A61B 90/70* (2016.01)

(52) U.S. Cl.
CPC .............. *A61B 8/12* (2013.01); *A61B 8/4254* (2013.01); *A61B 8/4444* (2013.01); *A61B 8/4472* (2013.01); *A61B 90/70* (2016.02)

(58) Field of Classification Search
CPC ......... A61B 8/12; A61B 8/4444; A61B 90/70; A61B 8/4472; A61B 8/4254
See application file for complete search history.

(56) References Cited

U.S. PATENT DOCUMENTS

| 5,377,682 A | * | 1/1995 | Ueno | ........................ | A61B 8/12 600/446 |
| 2003/0181788 A1 | * | 9/2003 | Yokoi | ................... | A61B 5/4839 600/160 |
| 2004/0254458 A1 | * | 12/2004 | Govari | .................... | A61B 34/20 600/437 |
| 2004/0260273 A1 | * | 12/2004 | Wan | ........................ | A61B 34/70 606/1 |
| 2010/0198008 A1 | * | 8/2010 | Kawano | ............. | A61B 1/00183 600/109 |
| 2012/0073614 A1 | * | 3/2012 | Otani | ...................... | A61B 1/121 134/56 R |
| 2012/0108942 A1 | * | 5/2012 | Boutet | ................. | A61B 5/0084 600/407 |
| 2021/0030394 A1 | * | 2/2021 | Caswell | ................... | A61B 8/56 |

* cited by examiner

*Primary Examiner* — Christopher Koharski
*Assistant Examiner* — Taylor Deutsch
(74) *Attorney, Agent, or Firm* — Nath, Goldberg & Meyer; Joshua B. Goldberg

(57) ABSTRACT

The present disclosure provides an ultrasonic probe assembly and a method using the same. The ultrasonic probe assembly includes: a handle and a probe body separable from the handle; wherein the handle is configured to control movement of the probe body in a body of an examinee; the probe body includes an ultrasonic component for emitting ultrasonic waves to the body of the examinee and receiving reflected ultrasonic waves to generate examination information, and a driving component for driving the ultrasonic component to move to change a direction of the ultrasonic waves emitted by the ultrasonic component.

15 Claims, 2 Drawing Sheets

ULTRASOUND PROBE ASSEMBLY AND METHOD USING THE SAME

CROSS-REFERENCE TO RELATED APPLICATION

This application claims the priority of China Patent Application No. 201821769998.1, filed to the China National Intellectual Property Administration (CNIPA) on Oct. 30, 2018, the entire contents of which are hereby incorporated by reference.

TECHNICAL FIELD

The present disclosure belongs to the technical field of medical devices, and in particular, to an ultrasound probe assembly and a method using the same.

BACKGROUND

The unique efficacy of ultrasound technology in medical treatment has been widely recognized by the medical community and is increasingly being valued and adopted by the clinic. Domestic and foreign medical experts have used ultrasound technology to achieve a great therapeutic effect in the treatment of soft tissue injury and limb movement, and extended ultrasound therapy to internal medicine, gynecology and the like. The ultrasound technology has been widely used in clinical practice and achieved satisfactory therapeutic effects.

SUMMARY

An aspect of the present disclosure provides an ultrasonic probe assembly including: a handle and a probe body separable from the handle; wherein the handle is configured to control movement of the probe body in a body of an examinee; the probe body includes an ultrasonic component for emitting ultrasonic waves to the body of the examinee and receiving reflected ultrasonic waves to generate examination information, and a driving component for driving the ultrasonic component to move to change a direction of the ultrasonic waves emitted by the ultrasonic component.

Optionally, the driving component includes an eccentric and a rotating mechanism that drives rotation of the eccentric, and the ultrasonic component is coupled to the eccentric.

Optionally, the probe body further includes a first magnetic component; the handle includes a second magnetic component that cooperates with the first magnetic component, and a repulsive force or attractive force can be generated between the first magnetic component and the second magnetic component.

Optionally, the first magnetic component and the second magnetic component are both electromagnetic units that generate magnetism using electrical energy.

Optionally, the probe body further includes: an outer casing having an outer surface that is a smooth surface, wherein the driving component and the ultrasonic component are both located within the outer casing.

Optionally, the outer casing is configured in a shape of connecting hemispherical surfaces at both ends of a cylinder.

Optionally, the probe body further includes: a heating component for heating the outer casing.

Optionally, the probe body further includes: a sensor for detecting a position of the probe body.

Optionally, the probe body further includes: a transmitting component for sending at least the examination information in a wireless manner.

Optionally, the probe body further includes: a battery for supplying electrical energy to the probe body.

Optionally, the handle has an engagement slot that matches a shape of at least a portion of the outer casing.

Optionally, the handle is configured to charge the probe body when the probe body is in contact with the handle.

Another aspect of the present disclosure provides a method using an ultrasonic probe assembly including: inserting a probe body attached on a handle into a body of an examinee, and separating the probe body from the handle; controlling movement of the probe body in the body of the examinee with the handle; and driving the ultrasonic component to move via the driving component such that the ultrasonic component emits or receives ultrasonic waves in different directions.

Optionally, the method using an ultrasonic probe assembly further includes: after an examination is completed, taking the probe body out of the body of the examinee by the handle under an action of an attracting force of the handle on the probe body.

Optionally, the method using an ultrasonic probe assembly further includes: after the probe body is taken out of the body of the examinee, placing the probe body in a cleaning device to clean the probe body, and forming a protective film on the probe body having been cleaned by a probe protection component.

DETAILED DESCRIPTION OF THE EMBODIMENTS

Figure 1:
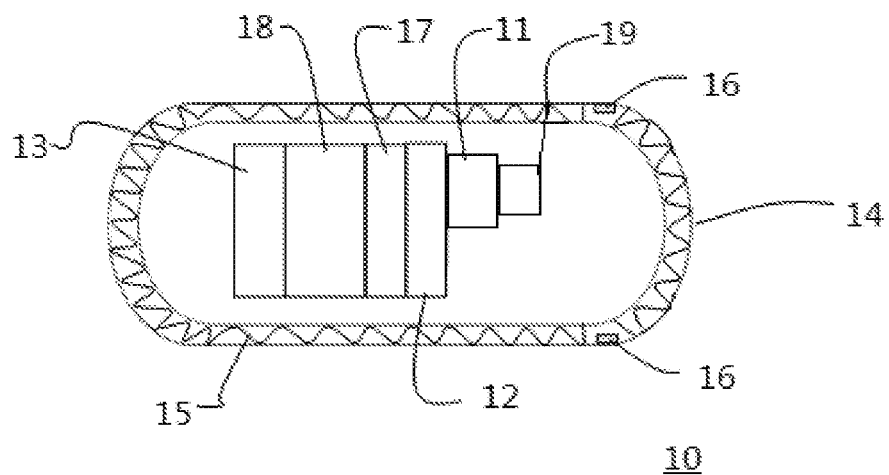
FIG. 1 is a schematic structural view of a probe body of an ultrasonic probe assembly according to an embodiment of the present disclosure.

The present disclosure will be described in more detail below with reference to the accompanying drawings. Throughout the drawings, the same elements are denoted by like reference numerals. For the sake of clarity, the various parts in the figures are not drawn to scale. Moreover, some well-known parts may not be shown in the figures.

Figure 2:
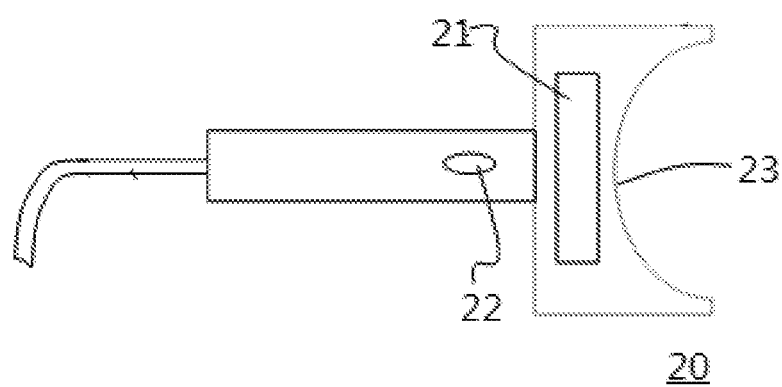
FIG. 2 is a schematic structural view of a handle of an ultrasonic probe assembly according to an embodiment of the present disclosure.
Figure 3A:
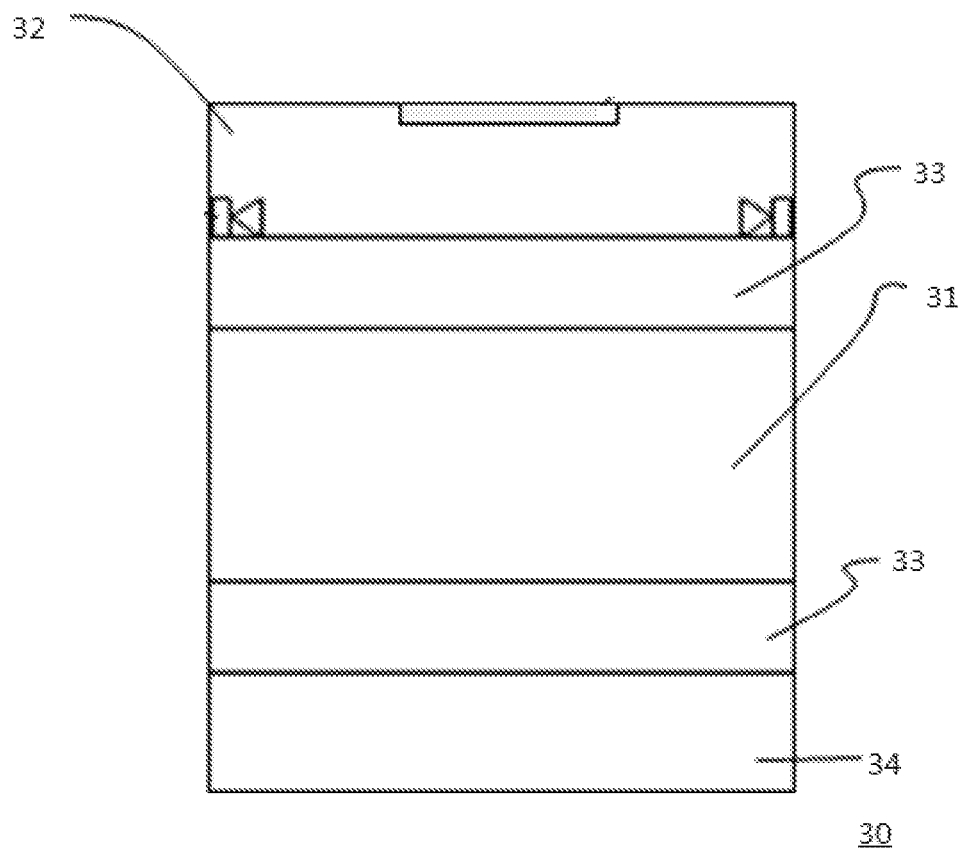
FIG. 3a is a schematic structural view of a cleaning device of an ultrasonic probe assembly according to an embodiment of the present disclosure.
Figure 3B:
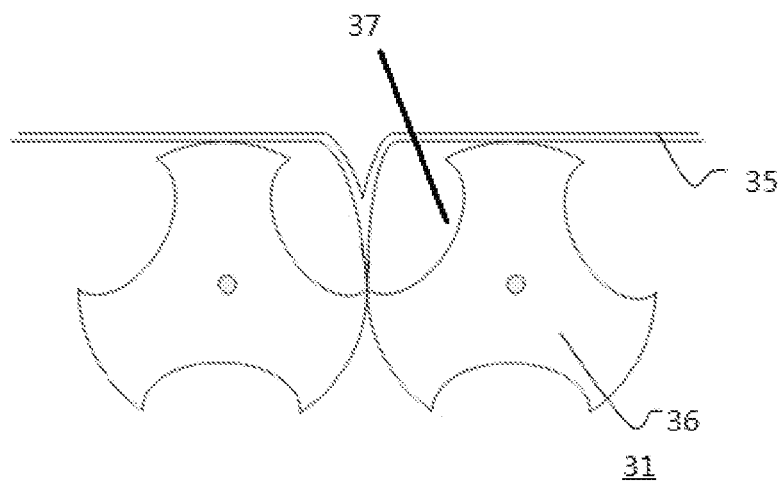
FIG. 3b is a schematic structural view of a probe protection component of a cleaning device of an ultrasonic probe assembly according to an embodiment of the present disclosure.

As shown in FIGS. 1-3, the present embodiment provides an ultrasonic probe assembly including: a handle 20 and a probe body 10 separable from the handle 20; wherein the handle 20 is configured to control movement of the probe body 10 in a body of an examinee;

the probe body 10 includes an ultrasound transducer and equivalents thereof 19 for emitting ultrasonic waves to the body of the examinee and receiving reflected ultrasonic waves to generate examination information, and a driving component for driving the an ultrasound transducer and equivalents thereof 19 to move to change a direction of the ultrasonic waves emitted by the an ultrasound transducer and equivalents thereof 19.

When the handle 20 and the probe body 10 are separated from each other, the handle 20 can also control the movement of the probe body 10 in the body of the examinee so that the probe body 10 can reach a portion to be examined. The driving component of the probe body 10 allows the ultrasonic component 19 of the probe body 10 to emit or receive ultrasonic waves in different directions to inspect different parts of the examinee and generate examination information (for example, Color Doppler examination information, black and white B-ultrasound information, etc.). Specifically, the driving component can drive a direction of an emitting surface (also is a receiving surface) of the ultrasonic component 19 to change, so as to emit or receive ultrasonic waves in different directions.

Since the above probe body 10 can enter the body of the examinee to emit ultrasonic waves, the ultrasonic probe assembly can be an ultrasonic probe assembly for vaginal examination, rectal examination, and the like. In the ultrasonic probe assembly of the embodiment, during adjustment of a position of the probe body 10 or during the examination, the movement of the probe body 10 can be controlled by the handle 20 without requiring the hand of the medical staff to directly apply force to the probe body 10. Therefore, it is possible to prevent the medical staff from injuring the arm muscles due to the long-term holding of the ultrasonic probe, so that the ultrasonic treatment process is simple and easy to operate, and the position of the probe body 10 is ensured to be accurate.

Optionally, the eccentric and motor/rotator, and equivalents thereof includes an eccentric 11 and a motor/rotator, and equivalents thereof 12 that drives rotation of the eccentric 11, and the ultrasonic component 19 is coupled to the eccentric 11.

During the examination, the eccentric 11 is rotated driven by the motor/rotator, and equivalents thereof 12, thereby changing the direction in which the ultrasonic component 19 emits or receives ultrasonic waves. Here, the eccentric 11 may be plural, and under the action of a plurality of different eccentrics 11, the ultrasonic component 19 may be allowed to emit or receive ultrasonic waves in more directions.

The eccentric 11 in the probe assembly can not only ensure smooth progress of the ultrasonic examination, but also a structure of the probe assembly is simple and easy to implement, so that manufacturing cost of the ultrasonic probe assembly can be reduced.

Optionally, the probe body 10 further includes a first magnetic component 13; the handle 20 includes a second magnetic component 21 that cooperates with the first magnetic component 13, and a repulsive force or attractive force can be generated between the first magnetic component 13 and the second magnetic component 21.

In the embodiment of the present application, optionally, before the examination is started, the attractive force may be generated between the first magnetic component 13 and the second magnetic component 21. At this time, the probe body 10 is attached on the handle 20, and the probe body is pushed into the body of the examinee by the handle 20. Thereafter, the repulsive force is generated between the first magnetic component 13 and the second magnetic component 21. The probe body 10 separated from the handle 20 can be moved to the portion to be examined by the repulsive force, that is, the handle 20 pushes the probe body 10 (by magnetic force) to the portion to be examined in the body of the examinee. During the examination, under the driving of the rotating mechanism 12, the eccentric 11 will rotate, thereby changing the direction in which the ultrasonic component 19 emits or receives ultrasonic waves. After the examination, the attractive force between the first magnetic component 13 and the second magnetic component 21 can attract the probe body 10 from the body of the examinee, that is, the handle 20 draws the probe body 10 out of the body of the examinee. Further, the handle 20 is provided with a switch 22 that controls switching on and off of the first magnetic component 13 and the second magnetic component 21.

The arrangement of the first magnetic component 13 and the second magnetic component 21 can realize the control of the handle 20 to the probe body 10, and such arrangement is simple and easy to operate.

Optionally, the first magnetic component 13 and the second magnetic component 21 are both electromagnetic units that generate magnetism using electrical energy.

That is, each of the first magnetic component 13 and the second magnetic component 21 may be an electromagnet. By controlling a direction of current applied to the first magnetic component 13 or the second magnetic component 21, the first magnetic component 13 and the second magnetic component 21 may attract or repel to each other.

Optionally, during the examination, the first magnetic component 13 and the second magnetic component 21 are switched off, so that no attractive force or repulsive force is generated between the handle 20 and the probe body 10, so as to avoid affecting ultrasonic signal.

The method of changing magnetic properties of electromagnetic units is simple and easy to operate, which makes the entire ultrasonic examination process easy to operate, thereby improving the work efficiency of the medical staff.

Optionally, the probe body 10 further includes an outer casing 14 having an outer surface that is a smooth surface, and the driving component and the ultrasonic component 19 are both located within the outer casing 14.

The handle 20 for controlling the probe body 10 can also have an engagement slot 23 that matches a shape of at least a portion of the outer casing 14 to allow the handle 20 to more stably attract the probe body 10.

Since the outer surface of the outer casing 14 is in direct contact with the body of the examinee during the ultrasonic examination, when the outer surface of the outer casing 14 has a smooth surface, discomfort due to the probe body 10 in the body of the examinee can be reduced.

Optionally, the outer casing 14 is configured in a shape of connecting hemispherical surfaces at both ends of a cylinder.

The handle 20 for controlling the probe body 10 has a hemispherical engagement slot 23, and one end of the outer casing 14 just snaps into the engagement slot 23.

Compared with a rod-shaped probe in prior art, the probe body 10 having the outer casing 14 of this shape can further reduce the discomfort due to the probe body 10 in the body of the examinee, thereby reducing the pain of treatment.

Optionally, the probe body 10 further includes a heating component 15 for heating the outer casing 14.

The heating component 15 can be disposed on an inner surface of the outer casing 14 or embedded in the outer casing 14. During the examination, the heating component 15 can heat the outer casing 14 to an internal temperature of the examinee. The heating component 15 referred to herein may be a heating wire or other suitable heating element.

The heating component 15 can heat the outer casing 14 in direct contact with the body of the examinee to an internal temperature of the examinee, thereby reducing the discomfort of the examinee during the examination.

Optionally, the probe body 10 further includes a sensor 16 for detecting a position of the probe body.

For example, during the examination, the sensor 16 can transmit position information of the probe body 10 obtained by the sensor 16 to a control terminal outside the body of the examinee. The control terminal can determine a specific position of the probe body 10 in the body of the examinee by analyzing the information sent by the sensor 16, so as to determine whether the probe body 10 reaches the portion to be examined.

By providing the sensor 16, the probe body 10 can be autonomously positioned to the specific portion to be examined, thereby avoiding manual search of the examination site, making the entire ultrasonic examination process simple and easy to operate.

Optionally, the probe body 10 further includes a transmission circuit and equivalents thereof 17 for sending at least the examination information in a wireless manner.

The examination information herein may include image information, text information, or other forms of information obtained by the examination. The transmitting component 17 can be disposed within the outer casing 14 of the probe body 10.

The transmitting component 17 is configured to transmit the information obtained by the examination to an external device (for example, a computer) connected by signal and located outside the body of the examinee, so that examination result can be analyzed in time or whether the examination is successful can be checked, so that the ultrasonic examination may proceed smoothly.

Optionally, the probe body 10 further includes a battery 18 for supplying electrical energy to the probe body 10.

The battery 18 can be disposed within the outer casing 14 of the probe body 10, which can be a storage battery or a conventional battery.

The battery 18 can continuously supply power to the probe body 10 during the examination to ensure that the probe body 10 separated from the handle 20 can perform the examination smoothly.

When the probe body 10 is in contact with the handle 20, the handle can also charge the probe body 10, thereby ensuring that the handle 20 can charge the inactive probe body 10 at any time.

Optionally, the ultrasonic probe assembly of the present embodiment further includes a cleaning device 30 including a probe protection component 31 for forming a seamless protective film 35 outside the probe body 10.

The cleaning device 30 is mainly used to clean the probe body 10 after completion of the ultrasonic examination. The probe protection component 31 of the cleaning device 30 forms a seamless protective film 35 on the surface of the probe body 10 after a preliminary cleaning (such as high-temperature water washing or ultraviolet irradiation) is completed. The protective film 35 is disposable, and the previous protective film 35 is removed after each examination is completed, so as to form a new protective film 35. A material forming the protective film 35 may be latex, polyurethane, novel composite nano, super material graphene, or any other suitable materials.

The protective film 35 formed on the outer surface of the probe body 10 is a seamless protective film 35, which avoids contamination of the probe body 10 due to peeling of the protective film 35 with slit in the prior art, and thereby possibly preventing disease spread.

Optionally, the probe protection component 31 includes two rotating wheels 36 axially parallel to each other. The rotating wheel 36 has a groove 37 on a side surface thereof.

The two rotating wheels 36 are rotatable relative to each other such that two grooves 37 on the two rotating wheels 36 pairs. An accommodating space formed by the two paired grooves 37 is closed and the probe body 10 can be accommodated therein.

Firstly, the probe body 10 is placed close to the two rotating wheels 36 paired with each other, and the protective film 35 to be attached is placed between the two rotating wheels 36 and the probe body 10; secondly, in a process of rotating the two rotating wheels 36 till the grooves 37 are paired, the probe body 10 and the protective film 35 are gradually placed in the accommodating space formed by the two paired grooves 37 as the rotation moves, so that the protective film 35 wraps the probe body 10; finally, the respective end of the two paired grooves 37 contacting with each other at last will seal an opening of the protective film 35 encasing the probe body 10, so as to form a seamless protective film 35.

The arrangement structure of the probe protection component 31 is simple and easy to implement, and the seamless protective film 35 can be quickly formed on the probe body 10.

Optionally, the cleaning device 30 further includes a cleaning and disinfecting component 32, and the cleaning and disinfecting component 32 includes a hydraulic sprayer and an ultraviolet lamp.

The hydraulic sprayer can spray a high-temperature cleaning liquid to achieve cleaning and sterilization of the probe body 10.

Optionally, the cleaning device 30 further includes a coupling coating component 33 for applying a couplant on the probe body 10.

Specifically, the couplant coating is performed according to requirements of the actual ultrasonic examination, and the couplant may be coated in two treatments or in single one treatment.

In addition, the cleaning device 30 also includes a storage unit 34 for storing the probe body 10.

An aspect of the present disclosure also provides a method using an ultrasonic probe assembly including: inserting a probe body 10 attached on a handle 20 into a body of an examinee, and separating the probe body 10 from the handle 20; controlling movement of the probe body 10 in the body of the examinee with the handle 20; and driving the ultrasonic component 19 to move via the driving component such that the ultrasonic component 19 emits or receives ultrasonic waves in different directions.

Further, the method also includes: after an examination is completed, taking the probe body 10 out of the body of the examinee by the handle 20 under an action of an attracting force of the handle 20 on the probe body 10.

Further, the method also includes: after the probe body 10 is taken out of the body of the examinee, placing the probe body 10 in a cleaning device 30 to clean the probe body 10, and forming a protective film on the probe body 10 having been cleaned by a probe protection component 31.

The method using an ultrasonic probe assembly in the above embodiment is as follows:

S10. Inserting a probe body 10 attached on a handle 20 into the body of the examinee.

S20. Switching on the first magnetic component 13 located at the probe body 10 and the second magnetic component 21 located at the handle 20 respectively to generate a repulsive force therebetween; and moving the probe body 10 to the portion to be examined in the body of the examinee under the action of the repulsive force of the handle 20 on the probe body 10.

S30. Switching off the first magnetic component 13 and the second magnetic component 21 so as not to generate a force therebetween.

S40. Controlling the rotating mechanism 12 by a processor to drive the eccentric 11 to rotate, and finally driving the ultrasonic component 19 to emit or receive ultrasonic waves in different directions; and transmitting data obtained by the sensor 16, via the transmitting component 17, to the control terminal outside the body of the examinee.

S50. After the examination is completed, switching on the first magnetic component 13 and the second magnetic component 21 to generate an attractive force therebetween; and taking the probe body 10 out of the body of the examinee by the handle 20 under the action of the attracting force of the handle 20 on the probe body 10.

S60. Placing the probe body 10 in the cleaning device 30 to clean the probe body, and forming a new protective film 35 outside the outer casing 14 of the probe body 10 having been cleaned by a probe protection component 31.

In the embodiment of the present application, the examinee may be a human body, or may be an animal or the like who needs to perform ultrasonic examination, and is not limited in the present application.

It should be noted that, in this context, relational terms such as first and second and the like are used merely to distinguish one entity or operation from another entity or operation. There is no requirement or implied that there is any such actual relationship or order between these entities or operations. Furthermore, the term "comprise" or "include" or any other variations thereof is intended to encompass a non-exclusive inclusion, such that a process, method, item, or device that comprises a plurality of elements includes not only those elements but also other elements that are not explicitly listed, or elements that are inherent to such a process, method, item, or device. Without further limitation, an element defined by the phrase "comprising a . . . " does not exclude the presence of additional identical elements in the process, method, item, or device that comprises the element.

The embodiments according to the present disclosure are not described in all details in the above description, and are not intended to limit the present disclosure to the specific embodiments described above. Apparently, many modifications and variations are possible in light of the above description. These embodiments are chosen and described in detail in this specification in order to better explain the principles and practical applications of the present disclosure, so that the skilled person can make good use of the present disclosure and modify it on the basis of the present disclosure. This disclosure is limited only by the claims and the full scope and equivalents thereof.

What is claimed is:

1. An ultrasonic probe assembly comprising: a handle and a probe body separable from the handle; wherein
   the handle is configured to control movement of the probe body in a body of an examinee;
   the probe body comprises an ultrasonic component for emitting ultrasonic waves to the body of the examinee and receiving reflected ultrasonic waves to generate examination information, and a driving component for driving the ultrasonic component to move to change a direction of the ultrasonic waves emitted by the ultrasonic component,
   wherein the probe body further comprises a first magnetic component;
   the handle comprises a second magnetic component that cooperates with the first magnetic component, and a repulsive force can be generated between the first magnetic component and the second magnetic component, the probe body separated from the handle can be moved to a portion to be examined by the repulsive force,
   the ultrasonic probe assembly comprises a cleaning device comprising a probe protection component, the probe protection component comprises two rotating wheels axially parallel to each other, each rotating wheel has a groove on a side surface thereof, the two rotating wheels are rotatable relative to each other such that two grooves on the two rotating wheels pairs, an accommodating space formed by the two paired grooves is closed and the probe body is accommodated therein,
   wherein, the probe body is placed close to the two rotating wheels paired with each other, and a protective film to be attached is placed between the two rotating wheels and the probe body; in a process of rotating the two rotating wheels till the grooves are paired, the probe body and the protective film are gradually placed in the accommodating space formed by the two paired grooves as the rotation moves, so that the protective film wraps the probe body; respective ends of the two paired grooves contacting with each other at last will seal an opening of the protective film encasing the probe body, so as to form a seamless protective film.

2. The ultrasonic probe assembly according to claim 1, wherein the driving component comprises an eccentric and a rotating mechanism that drives rotation of the eccentric, and the ultrasonic component is coupled to the eccentric.

3. The ultrasonic probe assembly according to claim 1, wherein an attractive force can be generated between the first magnetic component and the second magnetic component.

4. The ultrasonic probe assembly according to claim 3, wherein the first magnetic component and the second magnetic component are both electromagnetic units that generate magnetism using electrical energy.

5. The ultrasonic probe assembly according to claim 4, wherein the probe body further comprises:
   an outer casing having an outer surface that is a smooth surface, wherein the driving component and the ultrasonic component are both located within the outer casing.

6. The ultrasonic probe assembly according to claim 5, wherein the outer casing is configured in a shape of connecting hemispherical surfaces at both ends of a cylinder.

7. The ultrasonic probe assembly according to claim 5, wherein the probe body further comprises:
   a heating component for heating the outer casing.

8. The ultrasonic probe assembly according to claim 7, wherein the probe body further comprises:
   a sensor for detecting a position of the probe body.

9. The ultrasonic probe assembly according to claim 8, wherein the probe body further comprises:
   a transmitting component for sending at least the examination information in a wireless manner.

10. The ultrasonic probe assembly according to claim 9, wherein the probe body further comprises:
    a battery for supplying electrical energy to the probe body.

11. The ultrasonic probe assembly according to claim 10, wherein the handle has an engagement slot that matches a shape of at least a portion of the outer casing.

12. The ultrasonic probe assembly according to claim 11, wherein the handle is configured to charge the probe body when the probe body is in contact with the handle.

13. A method using an ultrasonic probe assembly comprising:
   inserting a probe body attached on a handle into a body of an examinee, and separating the probe body from the handle,
   controlling movement of the probe body in the body of the examinee with the handle, and
   driving an ultrasonic component to move via a driving component such that the ultrasonic component emits or receives ultrasonic waves in different directions,
   wherein the probe body comprises a first magnetic component;
   the handle comprises a second magnetic component that cooperates with the first magnetic component, and a repulsive force can be generated between the first magnetic component and the second magnetic component, the probe body separated from the handle can be moved to a portion to be examined by the repulsive force,
   the ultrasonic probe assembly comprises a cleaning device comprising a probe protection component, the probe protection component comprises two rotating wheels axially parallel to each other, each rotating wheel has a groove on a side surface thereof, the two rotating wheels are rotatable relative to each other such that two grooves on the two rotating wheels pairs, an accommodating space formed by the two paired grooves is closed and the probe body is accommodated therein,
   wherein, firstly the probe body is placed close to the two rotating wheels paired with each other, and a protective film to be attached is placed between the two rotating wheels and the probe body; secondly, in a process of rotating the two rotating wheels till the grooves are paired, the probe body and the protective film are gradually placed in the accommodating space formed by the two paired grooves as the rotation moves, so that the protective film wraps the probe body; finally, respective ends of the two paired grooves contacting with each other at last will seal an opening of the protective film encasing the probe body, so as to form a seamless protective film.

14. The method using an ultrasonic probe assembly according to claim 13, further comprising:
   after an examination is completed, taking the probe body out of the body of the examinee by the handle under an action of an attracting force of the handle on the probe body.

15. The method using an ultrasonic probe assembly according to claim 14, further comprising:
   after the probe body is taken out of the body of the examinee, placing the probe body in the cleaning device to clean the probe body, and forming the protective film on the probe body having been cleaned by the probe protection component.

* * * * *